United States Patent
Christensen (10) Patent No.: US 9,651,535 B2
(45) Date of Patent: May 16, 2017

(54) METHOD AND ARRANGEMENT FOR DETERMINING A FUEL QUALITY

(71) Applicant: VOLVO TRUCK CORPORATION, Göteborg (SE)

(72) Inventor: Magnus Christensen, Mölndal (SE)

(73) Assignee: Volvo Truck Corporation, Göteborg (SE)

(*) Notice: Subject to any disclaimer, the term of this patent is extended or adjusted under 35 U.S.C. 154(b) by 111 days.

(21) Appl. No.: 14/654,003

(22) PCT Filed: Jan. 8, 2013

(86) PCT No.: PCT/EP2013/000026
§ 371 (c)(1),
(2) Date: Jun. 19, 2015

(87) PCT Pub. No.: WO2014/108138
PCT Pub. Date: Jul. 17, 2014

(65) Prior Publication Data
US 2015/0330960 A1    Nov. 19, 2015

(51) Int. Cl.
*F02D 41/02* (2006.01)
*G01N 33/22* (2006.01)
(Continued)

(52) U.S. Cl.
CPC ......... *G01N 33/22* (2013.01); *F02D 19/0628* (2013.01); *F02D 19/0636* (2013.01);
(Continued)

(58) Field of Classification Search
CPC ..... F02D 2200/0602; F02D 2041/2058; F02D 2041/2055; F02D 2200/0611; F02D 41/02;
(Continued)

(56) References Cited

U.S. PATENT DOCUMENTS 5,485,822 A * 1/1996 Hirose ............... F02D 35/0007
                                                       123/357
5,848,581 A * 12/1998 Hirose ............... F02D 35/0007
                                                       123/357
(Continued)

FOREIGN PATENT DOCUMENTS

CN    102400804 A    4/2012
CN    102817729 A    12/2012
(Continued)

OTHER PUBLICATIONS

International Search Report (Aug. 21, 2013) for corresponding International App. PCT/EP2013/000026.
(Continued)

*Primary Examiner* — David A Rogers
(74) *Attorney, Agent, or Firm* — WRB-IP LLP (57) ABSTRACT

In a method and an arrangement for determining a fuel quality of a fuel for a combustion engine fuel is conveyed from a low pressure fuel tank to a high-pressure volume, and injected into at least one cylinder of the combustion engine. A control valve is provided for controlling directly or indirectly the amount of fuel injected into the at least one cylinder. An actual value of a timing signal of the control valve is compared to a reference value of the timing signal of the control valve and a fuel quality parameter is derived from a difference between the actual value and the reference value of the timing signal of the control valve and/or that a fuel quality parameter is derived from a gradient of the pressure increase during a build-up phase of the pressure in the high-pressure volume compared to a reference value of the gradient of the pressure increase in the high-pressure volume.

20 Claims, 8 Drawing Sheets (51) Int. Cl.
*F02M 45/00* (2006.01)
*F02D 41/40* (2006.01)
*F02D 41/38* (2006.01)
*F02D 19/06* (2006.01)
*F02D 41/00* (2006.01)

(52) U.S. Cl.
CPC ..... *F02D 19/0649* (2013.01); *F02D 19/0684* (2013.01); *F02D 41/0025* (2013.01); *F02D 41/3845* (2013.01); *F02D 41/401* (2013.01); *F02M 45/00* (2013.01); *F02D 19/0652* (2013.01); *F02D 2200/0602* (2013.01); *F02D 2200/0606* (2013.01); *F02D 2200/0612* (2013.01); *Y02T 10/36* (2013.01)

(58) Field of Classification Search
CPC ............ F02D 41/3827; F02D 41/3845; F02D 41/123; F02D 41/021
See application file for complete search history.

(56) References Cited

U.S. PATENT DOCUMENTS

| | | | | |
|---|---|---|---|---|
| 6,622,549 | B1* | 9/2003 | Wlodarczyk | F02D 35/022 73/114.16 |
| 6,688,279 | B2* | 2/2004 | Ishikawa | F02D 41/0057 123/299 |
| 7,726,284 | B2* | 6/2010 | Hori | F02D 41/2464 123/458 |
| 8,437,942 | B2* | 5/2013 | Nakata | F02D 41/3809 701/103 |
| 9,458,806 | B2* | 10/2016 | Zhang | F02D 41/3836 |
| 2005/0166891 | A1* | 8/2005 | Fukasawa | F02D 35/025 123/305 |
| 2006/0170909 | A1* | 8/2006 | Wlodarczyk | F02D 35/022 356/225 |
| 2014/0316681 | A1* | 10/2014 | Whitney | F02D 41/221 701/108 |
| 2014/0331642 | A1* | 11/2014 | Dearth | F02D 19/025 60/273 |
| 2014/0331668 | A1* | 11/2014 | Bidner | F02M 26/36 60/605.2 |
| 2015/0000631 | A1* | 1/2015 | Choi | F02D 41/402 123/305 |
| 2015/0144108 | A1* | 5/2015 | Kim | F02M 69/54 123/460 |
| 2015/0345409 | A1* | 12/2015 | Bollinger | F02D 41/2438 701/105 |
| 2016/0032853 | A1* | 2/2016 | Huang | F02D 41/14 701/107 |

FOREIGN PATENT DOCUMENTS

| | | |
|---|---|---|
| DE | 102 52 476 A1 | 5/2004 |
| DE | 10 2011 077404 A1 | 12/2012 |
| EP | 0 828 070 A2 | 3/1998 |
| EP | 1 873 378 A1 | 1/2008 |
| JP | H06229304 A | 8/1994 |
| JP | H07174040 A | 7/1995 |
| JP | H09126038 A | 5/1997 |
| JP | 2002227693 A | 8/2002 |
| WO | 02084101 A1 | 10/2002 |
| WO | 2009056402 A1 | 5/2009 |

OTHER PUBLICATIONS

International Preliminary Report on Patentability (May 22, 2015) for corresponding International App. PCT/EP2013/000026.
Chinese Official Action (Feb. 21, 2017) for corresponding Chinese Application 201380069885.4.

\* cited by examiner

METHOD AND ARRANGEMENT FOR DETERMINING A FUEL QUALITY

BACKGROUND AND SUMMARY

The invention relates to a method and an arrangement for determining a fuel quality of fuel for a combustion engine as well as to a computer program and a computer program product.

Biodiesel is a vegetable oil- or animal fat-based diesel fuel, made by chemically reacting alcohol with lipids from, by ways of example, rape seed oil, palm oil or soy oil, generating long-chain alkyl esters of methyl, propyl or ethyl. Biodiesel is used in standard diesel engines. In standard diesel engines equipped with injection pumps biodiesel can be used either unblended in pure form ("B100") or, alternatively, may be blended with mineral diesel fuel (petroleum diesel, petrodiesel) at any concentration. However, for instance, new high pressure (29,000 psi=200 MPa) common-rail diesel engines have strict factory limits of B5 or B20 (meaning a permitted maximum of 5 vol % and 20 vol % of biodiesel in the blend) depending on manufacturer.

Biodiesel can be used as fuel without altering the combustion engine. However, biodiesel as well as synthetic diesel have densities and specific caloric values different from petrodiesel. This may result in the necessity to alter the fuel quantity for instance in an injection system for achieving the same engine torque and same rotational speed when using varying fuels of fuel compositions. Altering the injected fuel quantity on the other hand may require an adaptation of control parameters of the engine control as this may influence the exhaust temperature as well as the exhaust composition.

For instance, the amount of soot generated in the engine as well as the content of nitrogen oxides is influenced by the fuel composition and may even be improved compared to petrodiesel, so that the exhaust regeneration has to be adapted, too. Typically, the engine calibration is usually not optimally adapted with respect to emissions, noise, fuel consumption and the like when such synthetic diesel or biodiesel fuel additives are used together with petrodiesel or, if petrodiesel is completely replaced, by such alternative fuels.

EP 2 080 888 A2 discloses a method for determining the quality of the fuel for a direct-injection internal combustion engine in a vehicle. The common-rail fuel injection system comprises a fuel pump which is controlled by a PID-regulator. When the fuel viscosity changes the I-value of the PID-regulator will change. It will also change in response to the modified viscosity and thus the modified rail pressure. Subsequently, the new viscosity can be determined using the new I-value in combination with reference values stored in a characteristic map. The evaluation of the viscosity of the fuel is performed during a stationary or a degressive operation mode of the combustion engine.

DE 102011077404 relates to a method for determining fuel quality in conjunction with a high-pressure injector, by analysing a pressure increase curve.

WO 2009056402 relates to a method for identifying a fuel type, using measurements of the pressure in a high-pressure area over time.

EP 0 828 070 and EP 1 873 378 relate to methods involving characterization of a fuel type using a pressure signal.

DE 102 52 476 relates to a method involving determination of a type of fuel, utilizing an analysis of the movement of a magnetic valve.

W002/084101 relates to a method involving determination of a value significant for the energy content of a fuel, utilizing the movement of a movable valve element.

It is desirable to provide a method and an arrangement for determining a fuel quality as fast and as accurately as possible with existing hardware in the vehicle.

According to a first aspect of the invention, a method is proposed for determining a fuel quality of a fuel for a combustion engine, particularly for a diesel engine, wherein the fuel is conveyed from a low-pressure fuel tank to a high-pressure volume and injected into at least one cylinder of the combustion engine, wherein a control valve is provided for controlling directly or indirectly the amount of fuel injected into the at least one cylinder. An actual value of a timing signal of the control valve is compared to a reference value of the timing signal of the control valve and a fuel quality parameter is derived from a difference between the actual value and the reference value of the timing signal of the control valve.

Additionally or alternatively, a fuel quality parameter is derived from a gradient of the pressure increase during a build-up phase of the pressure in the high-pressure volume compared to a reference value of the gradient of the pressure increase in the high-pressure volume.

Favourably, the method can be employed in common-rail injection systems as well as in unit-injector systems of diesel engines.

Expediently, the control valve can be a spill valve between the fuel tank and the high pressure volume—which is the common rail in a common rail injection system or a pump chamber in a fuel pump of a unit-injector system. The fuel quality parameter may be derived from a difference between the actual value and the reference value of the timing signal of a spill valve of a fuel supply system and/or from a difference between the actual value of the pressure gradient and a reference value of the pressure gradient in the fuel system.

Expediently, the fuel may be conveyed from the fuel tank at a first pressure to the high-pressure volume at a pressure higher than the first pressure and injected into at least one cylinder of the diesel engine, wherein the spill valve is provided for limiting the fuel pressure in the high-pressure volume.

In a favourable embodiment, a required pressure in the high-pressure volume is established via a closed loop control of the pressure by adjusting the control valve timing and/or its operating duration.

Expediently, the actual value of the timing signal of the control valve may be determined at constant engine torque. The accuracy of the determination of the control valve timing is improved by stable operation conditions of the engine.

In a further expedient embodiment, the actual value of the timing signal of the control valve may be refined with an actual value of the temperature of the fuel. Temperature dependencies of fuel density and fuel viscosity can be eliminated, thus improving the accuracy of the inventive method.

In a further favourable embodiment, the actual value of the pressure signal of the high-pressure volume may be refined with an actual value of the temperature of the fuel. Temperature dependencies of fuel density and fuel viscosity can be eliminated, thus improving the accuracy of the inventive method.

In a further expedient embodiment, the reference value of the timing signal of the control valve may be derived from a set of characteristic curves for a reference fuel. The reference fuel may be petrodiesel the parameters of which are well known.

Determining the quality of the fuel the invention advantageously solves the problem of measuring the composition of the fuel when running on pure biodiesel or pure synthetic diesel or a blend of diesel and synthetic diesel or biodiesel (e.g. RME; RME being a short form for rape seed biodiesel). An advantage is that no additional hardware is needed in the case of common-rail injection systems. In the case of unit-injector systems, it is expedient to couple a pressures sensor to the high-pressure volume.

The installation of an additional fuel sensor can be avoided which will reduce the total engine cost. The timing signal of the control valve can be easily derived from the control signals of the control unit controlling the operation of the control valve which, for instance in a common-rail diesel engine, can be the control unit controlling the operation of the various actuators in the common-rail arrangement (also called the rail controller). The timing signal is preferably an on-signal or an off-signal for the control valve. The activation of the spill valve in the case of a common-rail injector system is programmed (i.e. mapped) for all engine operating conditions and thus available in the respective control units.

The invention is particularly usable in a common-rail injection system where fuel is conveyed from a low pressure fuel tank to a common rail (the high pressure volume) at a high pressure before being injected into the at least one cylinder of the combustion engine.

In a common-rail diesel engine, fuel is conveyed from a low pressure fuel tank to a high-pressure volume, i.e. a common rail, and injected into the engine via the common rail. The spill valve can be understood as a pressure control valve. Rail pressure and injection duration determines the amount of fuel injected.

For instance, in a common-rail injection system the fuel pressure is generated by a plunger (piston) pump in a high pressure reservoir (which is called the rail). The pressure within the rail is adjustable via a spill valve control. For a given rail pressure and a given amount of fuel injected into the (engine) cylinder, a certain duty cycle of plunger pumping is needed. The pumping period is represented by a parameter called "duty cycle" used in the control unit (ECU) of the rail (the rail controller). In order to obtain the required rail pressure, a pressure sensor is placed in the rail, and the adjustment of the correct pressure is controlled via a closed loop control of the rail pressure by adjusting the timing and/or duration of the operation of the spill valve (in the following also described as the spill valve timing and/or its operation duration). This is favourably used to detect differences in physical fuel properties, such as viscosity and/or density of the fuel. If these properties of the fuel vary, the pumping work has to decrease or increase compared to pure petrodiesel, i.e. the duty cycle has to be changed. For instance, if the values of the viscosity and density of the actual fuel other than petrodiesel are lower than those for petrodiesel, the pumping period has to be increased correspondingly for such other fuel, and, consequently, has to be decreased, if the values of the viscosity and density of the actual fuel are higher than those for petrodiesel. The respective petrodiesel properties are well known and standardized and, therefore, can be utilized advantageously as reference properties.

Alternatively or additionally, the actual value of the timing signal of the control valve may be refined with an actual value of the pumping period of a fuel pump conveying the fuel from the fuel tank to the high-pressure volume such as the rail (particularly in a common-rail injection system). The accuracy and robustness of the method can be improved by including more signals for the determination of the actual value of the timing signal of the control valve.

The method is particularly also usable in a unit-injector system where the fuel is compressed in a pump volume while pumping is taking place during injection of the fuel into the at least one cylinder. Particularly, in a unit-injector diesel engine fuel is injected by needle valves in individual cylinders of the engine. A spill valve is provided between a fuel pump and a fuel tank. In case of a unit-injector system, the spill valve timing is equivalent to a specific crank angle position. The fuel quality parameter can be derived from the spill valve timing as well as from a gradient of a pressure during a build-up phase versus a spill valve timing (i.e. a crank angle position) in a high-pressure volume, particularly a pump chamber, during injection of the fuel.

The fuel quality parameter is derived from a gradient of the pressure increase during a build-up phase in the high-pressure volume compared to a reference value of the pressure signal of the high-pressure volume, particularly a pump chamber of a fuel pump.

In case of the unit-injector system, the activation of the spill valve is programmed (i.e. mapped) for all engine operating conditions and thus available in the respective control units such as a spill valve control. There is no common rail in such a system. The fuel pump compresses the fuel in the pump chamber, which is the high-pressure volume in case of the unit-injector system, and the fuel is injected into individual cylinders by needle valves arranged at each of the individual cylinders. Injection takes place while the pump is pumping fuel. The needle valve controls the fuel injection into the combustion chamber, the injection timing and the injection duration. In prior art systems, the fuel pressure is mapped in a control unit and, consequently, the fuel pressure is not measured. According to the invention, by coupling a pressure sensor to the high-pressure volume, i.e. the pump chamber of the fuel pump, a pressure can be determined in the pump chamber.

Expediently, in the unit-injector system the required pressure in the high-pressure volume is established via a closed loop control by adjusting the needle-opening pressure of an injector valve and/or by adjusting the actual value of the timing signal of the control valve and/or its operating duration.

Determining the quality of the fuel the invention advantageously solves the problem of measuring the composition of the fuel when running on pure biodiesel or pure synthetic diesel or a blend of diesel and synthetic diesel or biodiesel (e.g. RME; RME being a short form for rape seed biodiesel). The installation of an additional fuel sensor can be avoided which will reduce the total engine cost.

The pressure signal of the high-pressure volume can be easily derived from a pressure sensor coupled to the pump chamber, e.g. in the pump chamber or close to it, and submitted to a control unit controlling the operation of the control valve. For instance, for a unit-injector system, the injector pressure will be higher if the engine is run on biodiesel compared to the engine run on petrodiesel and the pressure can thus be monitored.

In case the required maximum pressure for injection is fixed, the pressure in the pump chamber of the fuel pump will increase faster for biodiesel than for petrodiesel. This is favourably used to detect differences in physical fuel properties, such as viscosity and/or density of different fuels. If these properties vary, the gradient of the pressure increase in the build-up phase of the pressure in the pump chamber is lower or higher compared to pure petrodiesel. The respective petrodiesel properties are well known and standardized and, therefore, can be utilized advantageously as reference properties. In a conventional unit-injector system, a steeper increase of the pressure would result in a higher pressure which could damage the unit injector.

According to a further aspect of the invention, an arrangement is proposed for performing a method for determining a fuel quality of a fuel for a combustion engine, particularly of a diesel engine, where the fuel is conveyed from a low-pressure fuel tank to a high-pressure volume and injected into at least one cylinder of the combustion engine, wherein a control valve is provided for controlling directly or indirectly the amount of fuel injected into the at least one cylinder. A control unit is provided for comparing an actual value of a timing signal of the control valve to a reference value of the timing signal of the control valve and deriving a fuel quality parameter from a difference between the actual value and the reference value of the timing signal of the control valve.

Additionally or alternatively, a fuel quality parameter is derived from a gradient of the pressure increase during a build-up phase of the pressure in the high-pressure volume compared to a reference value of the gradient of the pressure increase in the high-pressure volume.

This arrangement may be particularly suited for diesel engines with a common-rail injection system, or with a unit-injector system where the control valve can be the spill valve of the system which spill valve is used to limit the pressure in the high pressure volume.

In a favourable embodiment, a required injection pressure may be established via a closed loop control of the pressure by adjusting the control valve timing and/or its operating duration. In case of a unit-injector diesel engine the needle valves associated with the individual cylinders control the fuel injection into the combustion chamber, the injection timing and the injection duration.

Alternatively or additionally, the actual value of the pressure signal may be refined with an actual value of the pumping period of a fuel pump conveying the fuel from the fuel tank to the high-pressure volume such as the fuel pump chamber in a unit-injector system. The accuracy and robustness of the method can be improved by including more signals for the determination of the actual value of the pressure signal of the high-pressure volume.

Expediently, a temperature sensor may be provided for determining an actual value of the temperature of the fuel, thus improving the measurement accuracy of the method. Further, a pressure sensor may be provided for measuring the pressure and/or a pressure gradient in the high-pressure volume.

According to another aspect of the invention, a vehicle comprising an arrangement for performing a method for determining a fuel quality of a fuel for a combustion engine, particularly a diesel engine, is proposed, where the fuel is conveyed from a low pressure fuel tank and injected into at least one cylinder of the combustion engine, wherein a control valve is provided for controlling directly or indirectly the amount of fuel injected into the at least one cylinder. The vehicle may be equipped with a common-rail injection system. In this case, an actual value of a timing signal of the spill valve is compared to a reference value of a timing signal of the control valve and a fuel quality parameter is derived from a difference between the actual value and the reference value of the timing signal of the control valve.

Alternatively, the vehicle may be equipped with a unit-injector system where differences of the spill valve timing compared to a timing related reference value and/or differences in the gradient of a pressure increase during a build-up phase in a fuel pump chamber compared to a pressure-gradient related reference value are used to derive the fuel quality.

According to another aspect of the invention, a computer program is proposed comprising a computer program code adapted to perform a method or for use in a method for performing a method for determining a fuel quality of a fuel for a combustion engine when said program is run on a programmable microcomputer, where the method includes conveying fuel from a fuel tank and injecting the fuel into at least one cylinder of the combustion engine, wherein a control valve is provided for controlling directly or indirectly the amount of fuel injected into the at least one cylinder and wherein, for instance in case of a common-rail injection system, an actual value of a timing signal of the control valve is compared to a reference value of the timing signal of the control valve and a fuel quality parameter is derived from a difference between the actual value and the reference value of the timing signal of the control valve. Additionally or alternatively, differences in the gradient of a pressure during a build-up phase in a high-pressure volume may be used to derive the fuel quality. The computer program may be adapted to be downloadable to a control unit or one of its components when run on a computer which is connected to the internet.

According to a further aspect of the invention, a computer program product stored on a computer readable medium is proposed, comprising a program code for use in a method as described above on a computer.

BRIEF DESCRIPTION OF THE DRAWINGS

The present invention together with the above-mentioned and other objects and advantages may best be understood from the following detailed description of the embodiments, but not restricted to the embodiments, wherein is shown schematically.

DETAILED DESCRIPTION

In the drawings, equal or similar elements are referred to by equal reference numerals. The drawings are merely schematic representations, not intended to portray specific parameters of the invention. Moreover, the drawings are intended to depict only typical embodiments of the invention and therefore should not be considered as limiting the scope of the invention.

Figure 1:
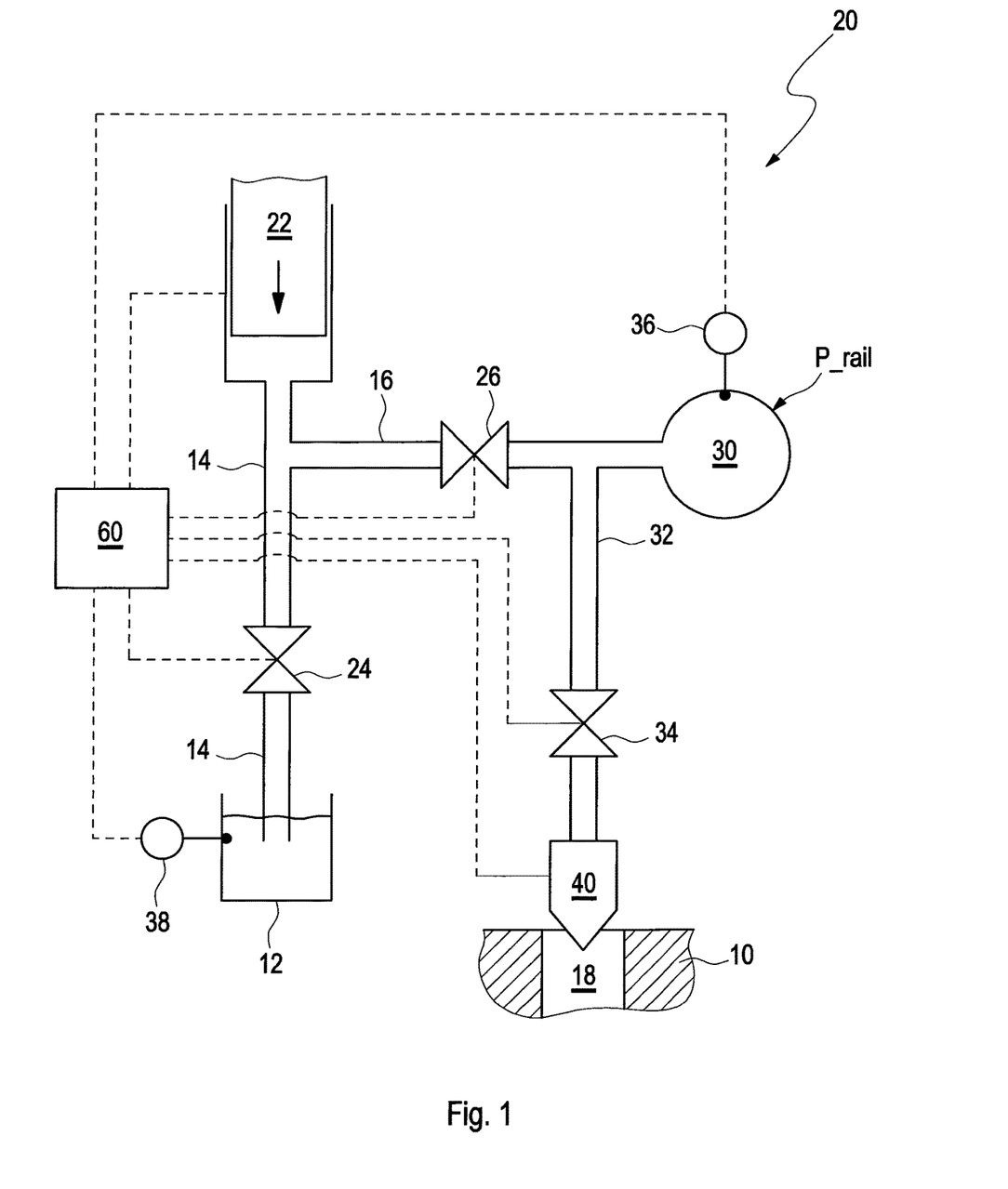
FIG. 1 an example embodiment according to the invention of a common-rail arrangement of a diesel engine for determining a timing signal of a control valve embodied as a spill valve in a common-rail injection system.

In FIG. 1 a schematic example embodiment of a common-rail injection system 20 is shown. A fuel pressure (p_rail in FIG. 2) is generated by a plunger (piston) of a pump 22 into a high-pressure volume 30, (which is also called "rail"), by conveying fuel from a low pressure fuel tank 12 to the high-pressure volume 30 through pipes 14 and 16. The fuel is conveyed from the fuel tank 12 to a pump chamber 22a of the pump 22 and then to the high-pressure volume 30. A control valve 24 (embodied as spill valve) is arranged as metering valve in pipe 14 between the fuel tank 12 and the pump 22. In pipe 16, a check valve 26 is arranged between the high-pressure volume 30 and the pump 22. A pressure sensor 36 is arranged at the high pressure side, e.g. at the high-pressure volume 30. The fuel is injected through injectors 40 into cylinders 18 of a diesel engine 10 (only one injector 40 and one cylinder 18 of the engine is shown by way of example), and a needle valve 34 is arranged in the connecting pipe 32 between the high-pressure volume 30 and the injector 40. The injector 40, the needle valve 34 and the pump 22 may be integrated into a single device or can be, in an alternative solution, separate devices.

The fuel tank 12 may contain one sort of fuel, for instance a blend of petrodiesel and synthetic or biodiesel. In an alternative solution (not shown in the Figure), there may be two or more separate reservoirs, one with petrodiesel and the other reservoir (or reservoirs) with biodiesel and/or synthetic diesel, whose outlets can be combined in order to mix the fuels of the reservoirs and to provide the wanted fuel mixture to the high-pressure volume. Alternatively, a multi-reservoir system (not shown in the Figure) can be provided wherein different fuels are stored in said reservoirs and wherein a valve control controls a valve arrangement connecting the individual outlets of the various reservoirs to the high-pressure volume in such a way that—at a time—fuel from only one reservoir is supplied to the high-pressure volume and that the individual fuel reservoirs can be connected consecutively to the high-pressure volume depending on needs of the engine that may change over the time in order to supply the engine with the right kind of fuel at the right time.

The fuel temperature can be detected by a temperature sensor 38 arranged at the fuel tank 12.

The components of the common-rail injection system 20 as well as preferably the engine 10 are controlled by a control unit 60, for instance an electronic control unit ECU. In the control unit 60, engine characteristic maps are stored by means of which—dependent for instance on control elements such as a gas pedal—the injectors 40 are controlled to inject fuel into the cylinders 18 required by e.g. a fuel demand of the driver. The actual pressure (p_rail in FIG. 2) in the high-pressure volume 30 is entered as input parameter and analyzed in the control unit 60, where the pressure p_rail can be dependent on the rotational speed of the engine 10, so that at higher rotational speeds a higher pressure p_rail is established in the high-pressure volume 30.

Other input parameters for the control unit 60 besides the actual pressure p_rail of the fuel in the rail are for instance fuel temperature, engine speed (particularly a signal relating to the actual crank angle), engine operational state (particularly a signal relating to an actual cam shaft position).

The pressure p_rail within the high-pressure volume 30 is adjustable via the control unit 60 controlling also the operation of the control valve 24. When the pressure p_rail has to be increased, the pump 22 conveys fuel from the fuel tank 12 to the high-pressure volume 30 through the control valve 24 which meters the fuel to be supplied to the high-pressure volume 30. When the required pressure is reached, excess fuel flows through the control valve 24 back to the fuel tank 12. The pressure p_rail in the high-pressure volume 30 is maintained by the check valve 26 and measured by a pressure sensor 36.

For a given rail pressure p_rail and amount of fuel injected into the (engine) cylinder 18, a certain duty cycle of plunger pumping of pump 22 is needed. This plunger pumping duty cycle is described by the pumping period (T_22 in FIG. 2). The pumping period T_22 is represented by a parameter called "duty cycle" used in the control unit 60 (ECU). In order to obtain the required rail pressure p_rail the adjustment of the correct pressure p_rail is controlled using the results of the pressure measurement with pressure sensor 36 via a closed loop control by adjusting the timing and/or duration of the control valve operation. This control is used to detect differences in physical fuel properties (particularly viscosity and density).

Figure 2:
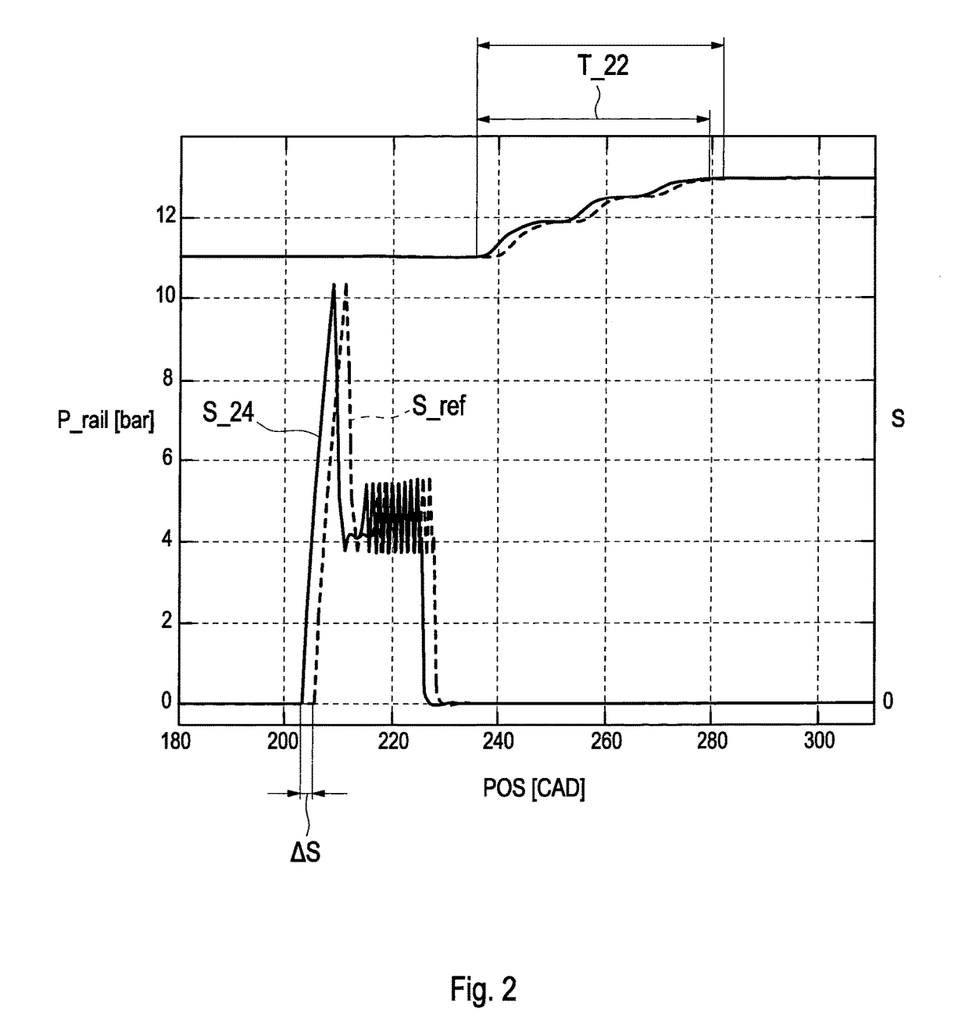
FIG. 2 a comparison of timing signals of a spill valve in a common-rail injection system for petrodiesel and for a fuel having a lower density and viscosity than petrodiesel for a system according to FIG. 1.
Figure 3:
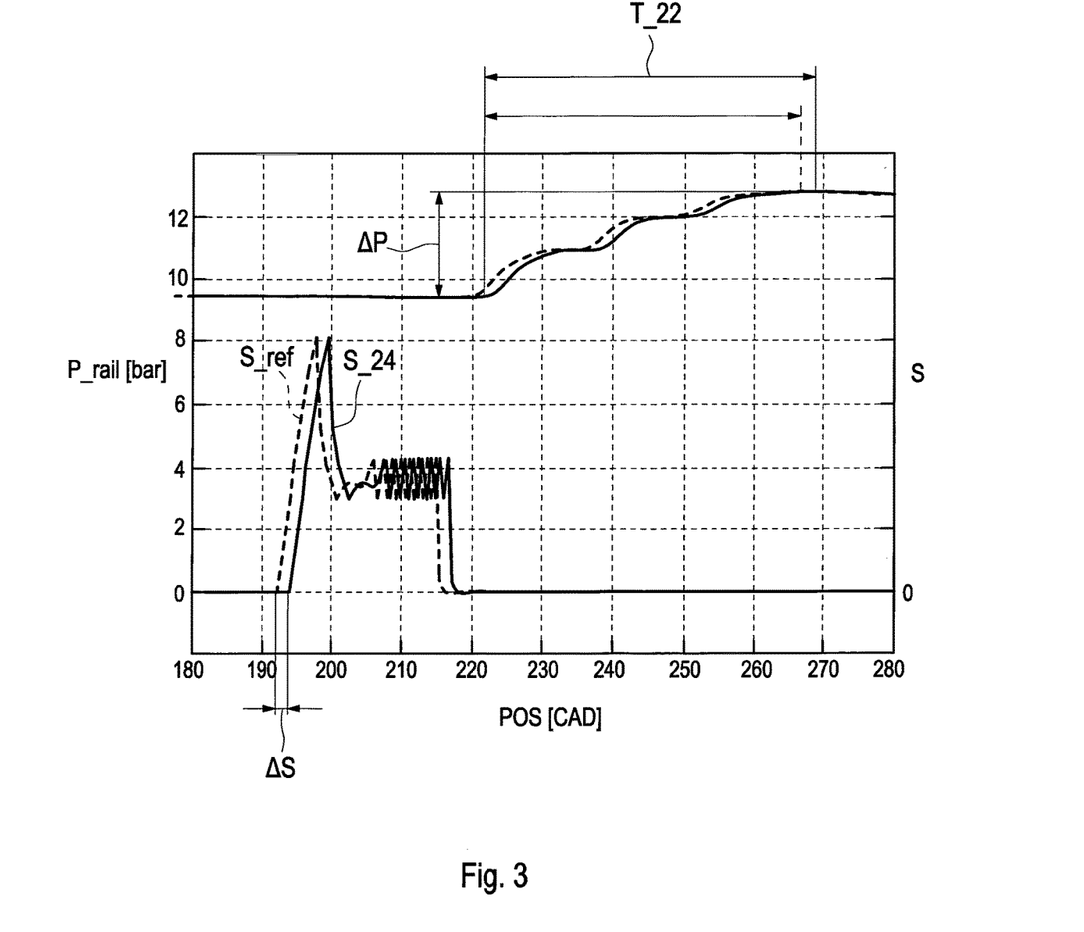
FIG. 3 a comparison of timing signals of a spill valve in a common-rail injection system for petrodiesel and a fuel having a higher density and viscosity than petrodiesel for a system according to FIG. 1.

If these properties vary, the pumping work has to be decreased or increased compared to pure petrodiesel, i.e. the "duty cycle" has to be changed. Accordingly, the control valve timing is used as a simple fuel sensor. For instance, if a fuel is used with a fuel viscosity and density values lower than those for petrodiesel, the pumping period T_22 has to be increased, as shown by way of example in FIG. 2. In FIG. 2 standard petrodiesel and synthetic diesel is compared with each other. In FIG. 2 the solid line graphs refer to synthetic diesel and broken line graphs refer to standard petrodiesel. Biodiesel (as for instance RME), on the other hand, has a much higher viscosity and density compared to standard petrodiesel, and will therefore require a shorter pumping period T_22. This is shown in FIG. 3. The higher the grade of RME blending is, the lower the "duty cycle", i.e. the pumping period, will be.

FIG. 2 shows a comparison of control valve timing signals of petrodiesel and a fuel having a lower density and viscosity than petrodiesel (as for example a synthetic diesel may have) as a function of the crank angle position of the engine in crank angle degrees CAD. A crank angle position of 360° CAD corresponds to the top dead centre TDC, which is the position farthest from the crankshaft of a piston in the engine 10. The control valve 24 (FIG. 1a) is a spill valve in this example.

The characteristics are shown for constant engine torque. As can be seen in the graph shown in the lower part of FIG. 2, the spill valve signal S_24 of the synthetic diesel starts earlier than the spill valve signal S ref for petrodiesel, resulting in a spill valve timing difference ΔS. In the graph shown in the upper part of FIG. 2, the rail pressure p_rail is indicated, showing the pressure increase Δp in the high-pressure volume 30 (FIG. 1) as well as the variation of the pumping duration T_22.

FIG. 3 shows a comparison of control valve timing signals of petrodiesel and a fuel having a higher density and viscosity than petrodiesel (as for example a biodiesel may have) as a function of the crank angle position of the engine. In FIG. 3 the solid line graphs refer to said biodiesel and broken line graphs refer to standard petrodiesel. The control valve is a spill valve in this example. As can be seen in the graph shown in the lower part of FIG. 3, the spill valve signal S_24 of the biodiesel starts earlier than the spill valve signal S_ref for petrodiesel, resulting in a spill valve timing difference AS. In the graph shown in the upper part of FIG. 3, the rail pressure p_rail is indicated, showing the pressure increase Δρ in the high-pressure volume 30 (FIG. 1) as well as the variation of the pumping period T_22.

Both Figures show that even for a small increase in rail pressure p_rail, the difference AS in the spill valve timing S_24 is noticeable, for instance in these examples about 2° crank angle per 80 bar. The spill valve timing controls the start of the pumping event of pump 22 (FIG. 1), i.e. when the spill valve 24 closes.

The spill valve (control valve 24) is open when it is not activated. The spill valve (control valve 24) is closed when it is activated, i.e. during pumping. This means that by activating the spill valve (control valve 24) the high-pressure volume 30 is closed so that a high pressure can be generated in the high-pressure volume 30.

Figure 4:
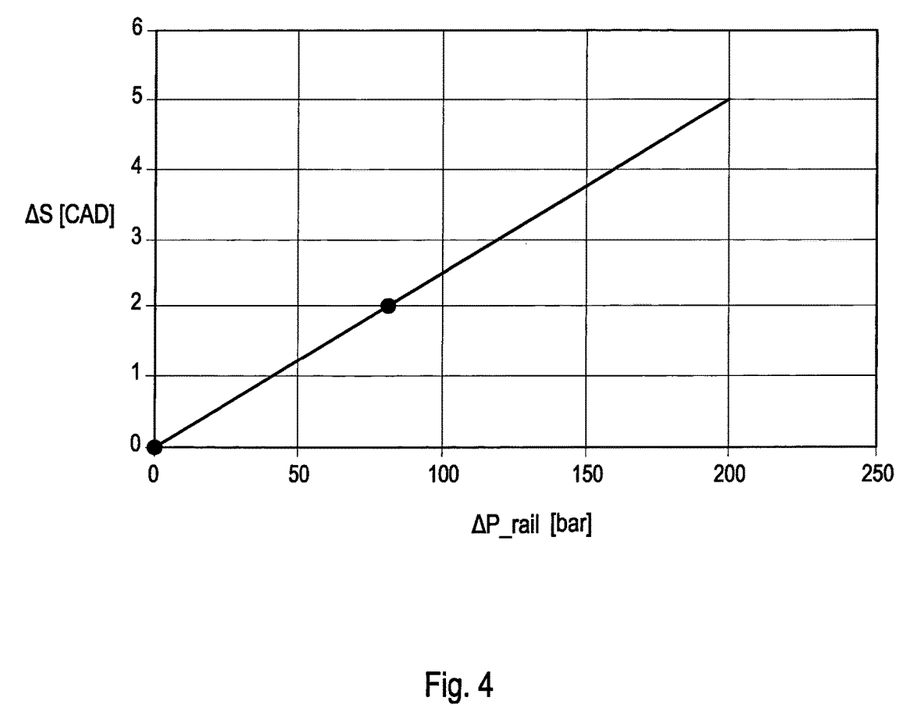
FIG. 4 a difference of a timing signal of a spill valve in a common-rail injection system versus a rail pressure increase according to the invention.

FIG. 4 illustrates by way of example a spill valve timing difference AS between petrodiesel and biodiesel versus an increase Δρ of the pressure in the rail, i.e. in the high-pressure volume (30 in FIG. 1). The difference means that the spill valve (control valve 24; FIG. 1) closes later (at a higher crank angle position) when biodiesel is used instead of petrodiesel.

Figure 5:
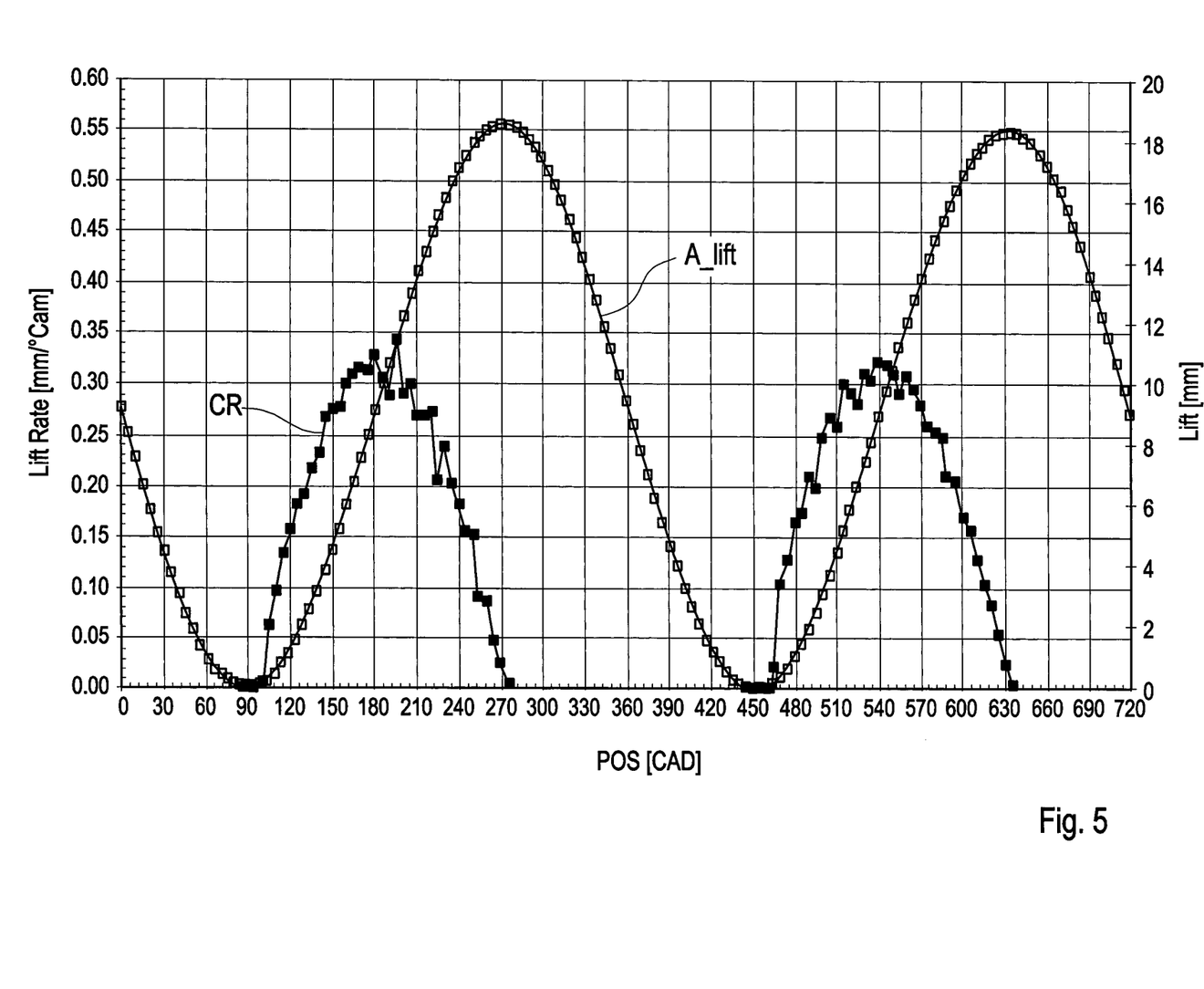
FIG. 5 a sinusoidal movement of a pumping element and a lift rate as a function of a crank angle position for a system according to FIG. 1.

FIG. 5 shows a sinusoidal movement of a pumping element referred to as AJift (in the graph of the Figure shown as Lift in mm—right hand vertical coordinate in the Figure) and two peaks referred to as CR with their respective maximum at the steepest positive slope of the sinusoidal curve showing the lift rate of the pumping element (in the graph of the Figure shown as mm/° Cam—left hand vertical coordinate in the Figure) as a function of a crank angle position POS shown in CAD (Crank Angle Degrees).

The pumping element, i.e. a plunger, of the pump 22 in FIG. 1, is for instance mechanically activated by a sinus-shaped profile of the cam shaft. This is indicated by graph AJift in FIG. 5, where the lift generated by the profile of the cam shaft is shown (in mm) as a function of the cam angle position CAD (in degrees). The pumping element's movement is independent of any control signal. When the lift of the plunger increases, i.e. the cam rate (graph CR in FIG. 5) is positive in a cam angle position range from approximately 90° to 270° and approximately 450° to 630° the fuel pressure can be increased, or, in other words pumping can occur. Pumping occurs two times per engine cycle. Fuel injection into the combustion chamber occurs in a range of approximately 350° to 380°, with a typical duration of approximately 5° to 25° crank angle position depending on power (torque) demand. The rotation speed of the cam shaft is proportional to the engine speed. The cam shaft rotates with half the rotational speed of the engine. Hence, FIG. 5 illustrates one cam shaft revolution.

If the spill valve (control valve 24 in FIG. 1) is not activated, no pressure increase or fuel pumping into the high-pressure volume 30 (rail or accumulator tank) will occur, the pumping element of pump 22 (FIG. 1) will just draw in fuel from the low pressure system, i.e. the low pressure fuel tank 12 in FIG. 1, when the pumping element moves up and then "put" it back into the low pressure system, i.e. the low pressure fuel tank 12 in FIG. 1. The pressure n the low pressure system is typically approximately at 5 bar. "Not activated" in this context means that the spill valve (control valve 24; FIG. 1) is open while "activated" means that the control valve 24 is closed.

The timing when the spill valve (control valve 24; FIG. 1) is activated, i.e. closed, determines the start of the pumping event and hence the duration of the pumping. The maximum pumping period is physically limited by the pump cam shaft profile, and in FIG. 5 the maximum duration can be approximately 1800 (×2 times) per cycle. So the control valve timing determines how much of the pumping is required in order to obtain a certain pressure increase of the high pressure tank 30.

Particularly for a common-rail injection system, the control valve timing and/or pumping period is a function of:

Fuel viscosity, as a higher viscosity gives more rapid pressure increase, i.e. spill valve timing is needed at a later point in time (more to the right on the crank angle position scale in FIG. 5), so that the spill valve is activated and deactivated at a later time;

Fuel density, as a higher density gives more rapid pressure increase, i.e. spill valve timing is needed at a later point in time (more to the right on the crank angle position scale in FIG. 5), so that the spill valve is activated and deactivated at a later time;

Fuel temperature, as a lower temperature gives more rapid pressure increase, i.e. spill valve timing is needed at a later point in time (more to the right on the crank angle position scale in FIG. 5), so that the spill valve is activated and deactivated at a later time, since viscosity and density increase as the fuel temperature increases;

Engine rotational speed (obtained from the crank signal), as the pumping is more effective at higher rotation speeds:

Desired pressure increase, as the desired pressure increase can depend on at least two conditions.

Firstly, if much fuel is injected into the combustion chamber (high engine torque), the pressure drop in the high-pressure volume (30 in FIG. 1) will be larger, and hence longer pumping period is needed to recapture this drop in pressure.

Secondly, the desired pressure change can also depend on the fact that the engine switches operating condition, and the wanted (optimum) injection pressure into the combustion chamber is a function of engine speed and torque.

The control unit 60 (FIG. 1) is arranged in a way to perform the inventive method by determining the actual value (S_24 in FIG. 2) of the timing signal of the spill valve (control valve 24 in FIG. 1) and comparing it to a reference value (S_ref in FIG. 2) of the timing signal of the spill valve (control valve 24 in FIG. 1). These reference values (control valve 24 in FIG. 1) are derived from fuel characteristics of well-known and standardized fuels such as for instance petrodiesel in order to derive from that comparison the actual quality of the fuel used in the fuel supply system for the high-pressure volume, i.e. the rail.

The control unit 60 may include a programmable microcomputer with a computer program code adapted to perform the method or which is used in the method when the program is run on the microcomputer. Particularly, the computer program is adapted to be downloadable to the control unit 60 or one of its components when the microcomputer is connected to the internet.

Optionally, a computer program product stored on a computer readable medium may comprise a program code for use in the method on the microcomputer.

The properties of the fuel injected into the engine 10 (FIG. 1) influences the exhaust temperature, the composition of the exhaust gas and the torque and power output of the engine 10. For instance, compared to petrodiesel, the density of synthetic diesel is lower, whereas the density of biodiesel is higher, while the viscosity of synthetic diesel is only slightly lower and the viscosity of biodiesel is much higher. These differences in viscosity and density determine the injection pressure of the injectors (40 in FIG. 1) that is needed to operate the engine in a proper way. The heating value (heat of combustion) of synthetic diesel is a little bit higher than that of petrodiesel, while biodiesel has a much lower heating value than petrodiesel. The fuel energy per liter for petrodiesel is higher than for synthetic diesel and for biodiesel the latter having the lowest fuel energy per liter of these three types of fuel. This is of importance for the torque and the power of the engine 10 (FIG. 1). When the fuel quality is known, the engine control can be adapted to operate the engine 10 (FIG. 1) as well as an exhaust gas treatment system associated with said engine 10 accordingly.

Figure 6:
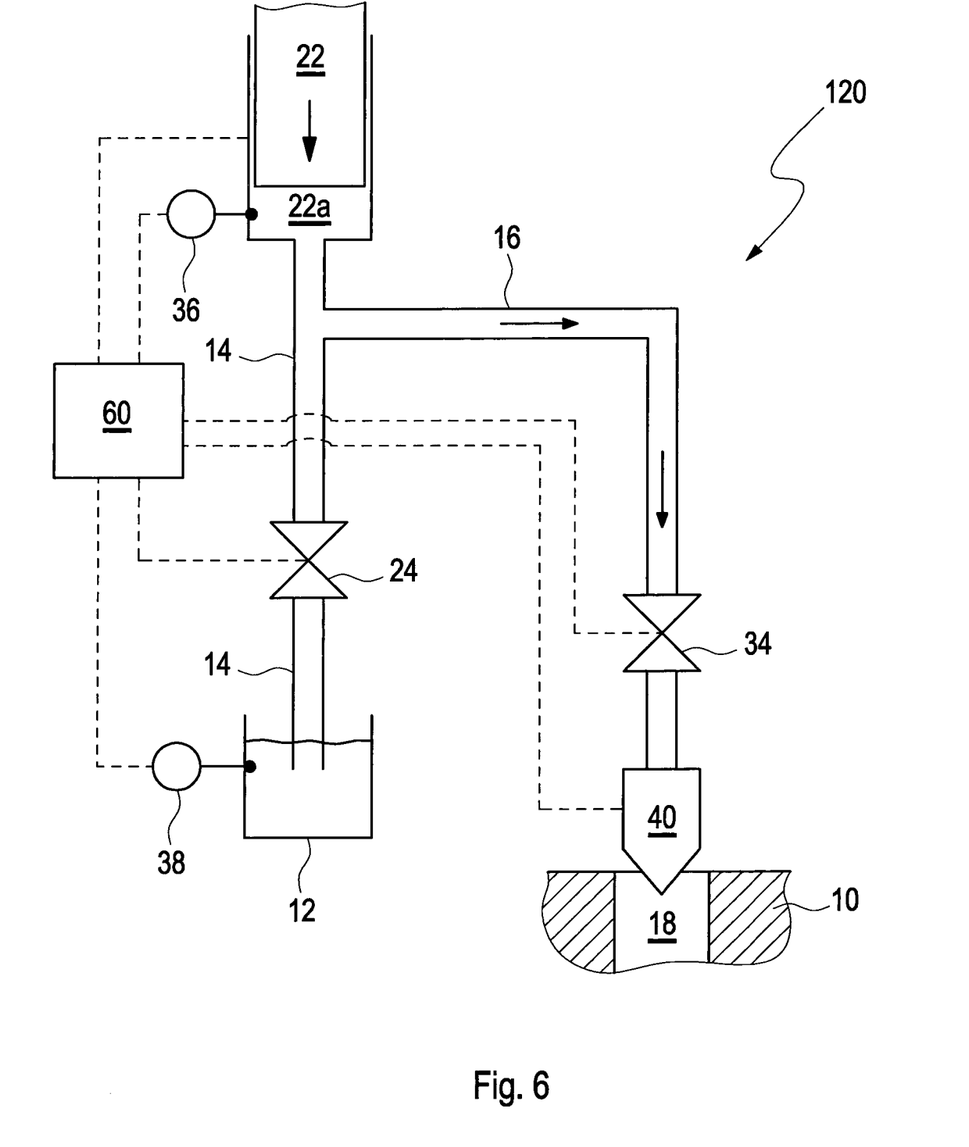
FIG. 6 an example embodiment according to the invention of an arrangement of a diesel engine for determining a timing signal of a control valve embodied as a needle valve in a unit-injector system.

FIG. 6 shows an example embodiment of an arrangement of a diesel engine 10 having a unit-injector system 120 with individual needle valves 34 for each cylinder 18 (only one is depicted in the Figure).

In the embodiment shown in FIG. 6 the fuel pressure (p_inj in FIG. 7) is generated by a plunger (piston) pump 22 in a pump chamber 22a of the pump 22, by conveying fuel from a low pressure fuel tank 12 to the pump chamber 22a through pipe 14 and a pipe 16 to the needle valve 34. A control valve 24 embodied as spill valve is arranged as metering valve in pipe 14 between the fuel tank 12 and the pump 22. A pressure sensor 36 is arranged at the pump 22 for determining the pressure in the pump chamber 22a. When the needle valves 34 is open, the fuel is injected through injectors 40 into cylinders 18 of the engine 10 (only one injector 40, one needle valve 34 and one cylinder 18 of the engine 10 are shown by way of example), and the needle valve 34 is arranged between the pump 22 and the injector 40. The injector 40, the needle valve 34 and the pump 22 may be integrated into a single device or can be, in an alternative solution, separate devices.

The fuel tank 12 may contain one sort of fuel, for instance a blend of petrodiesel and synthetic or biodiesel. In an alternative solution (not shown in the Figure), there may be two or more separate reservoirs, one with petrodiesel and the other reservoir (or reservoirs) with biodiesel and/or synthetic diesel, whose outlets can be combined in order to mix the fuels of the reservoirs and to provide the wanted fuel mixture to the high-pressure volume. Alternatively, a multi-reservoir system (not shown in the Figure) can be provided wherein different fuels are stored in said reservoirs and wherein a valve control controls a valve arrangement connecting the individual outlets of the various reservoirs to the high-pressure volume (i.e. the pump chamber 22a) in such a way that—at a time—fuel from only one reservoir is supplied to the high-pressure volume and that the individual fuel reservoirs can be connected consecutively to the high-pressure volume depending on needs of the engine that may change over the time in order to supply the engine with the right kind of fuel at the right time.

The fuel temperature can be detected by a temperature sensor 38 arranged at the fuel tank 12.

The components of the unit-injector injection system 120 as well as preferably the engine 10 are controlled by a control unit 60, for instance an electronic control unit ECU. In the control unit 60, engine characteristic maps are stored by means of which—dependent for instance on control elements such as a gas pedal—the injectors 40 are controlled to inject fuel into the cylinders 18 required by e.g. a fuel demand of the driver. The actual pressure (p_inj in FIG. 7) in the high-pressure volume, i.e. the pump chamber 22a in this embodiment, is entered as input parameter and analyzed in the control unit 60, where the pressure p_inj can be dependent on the rotational speed of the engine 10, so that at higher rotational speeds a higher pressure p_inj is established in the pump chamber 22a of pump 22.

For the unit-injector system, the pressure p_inj must always be increased, since at the start of every operating engine cycle, the fuel pressure is at low pressure circuit level (for instance ~5 bar). The operating cycle is as follows: When the plunger in the fuel pump 22 moves upwards, the pump chamber 22a will be filled up with fuel. When pump chamber 22a is fully filled, it is always filled with the same amount fuel. When the plunger starts to move downwards it puts out fuel into the low pressure circuit until the spill valve 24 is activated. As a result of this activation the build-up phase of the pressure pjnj in the pump chamber 22a starts, i.e. the pressure increases. The pump chamber 22a is in fluid connection to the needle valves 34 of the combustion engine 10. When a needle valve 34 opens the fuel is injected into the respective cylinder 18 of the engine 10. The fuel that is left in the pump chamber 22a after EOI (EOI=End Of Injection), is then flowing back into the low pressure circuit.

Other input parameters for the control unit 60 besides the actual pressure p_inj of the fuel in the pump chamber 22a are for instance fuel temperature, engine speed (particularly a signal relating to the actual crank angle), engine operational state (particularly a signal relating to an actual cam shaft position).

The pressure p_inj within the pump chamber 22a is adjustable via the control unit 60 controlling also the operation of the spill valve 24 and needle valve 34. When the pressure p_inj has to be increased, the pump 22 conveys fuel from the fuel tank 12 to the needle valve 34 through the spill valve 24 which meters the fuel to be supplied to the engine 10. When the required pressure is reached, excess fuel flows through the spill valve 24 back to the fuel tank 12.

For a given injection pressure p_inj and amount of fuel injected into the (engine) cylinder 18, a certain duty cycle of plunger pumping of pump 22 is needed. This plunger pumping duty cycle is described by the pumping period. The pumping period is represented by a parameter called "duty cycle" used in the control unit 60 (ECU). In order to obtain the required pressure the adjustment of the correct pressure pjnj is controlled using the results of the pressure measurement with pressure sensor 36 via a closed loop control by adjusting the timing and/or duration of the control valve operation. This control is used to detect differences in physical fuel properties (particularly viscosity and density).

If these properties vary, the pumping work has to be decreased compared to pure petrodiesel, i.e. the "duty cycle" has to be changed. Accordingly, the control valve timing is used as a simple fuel sensor. For instance, if a fuel is used with a fuel viscosity and density values higher than those for petrodiesel, the pumping period has to be increased, as shown by way of example in FIG. 7.

Figure 7:
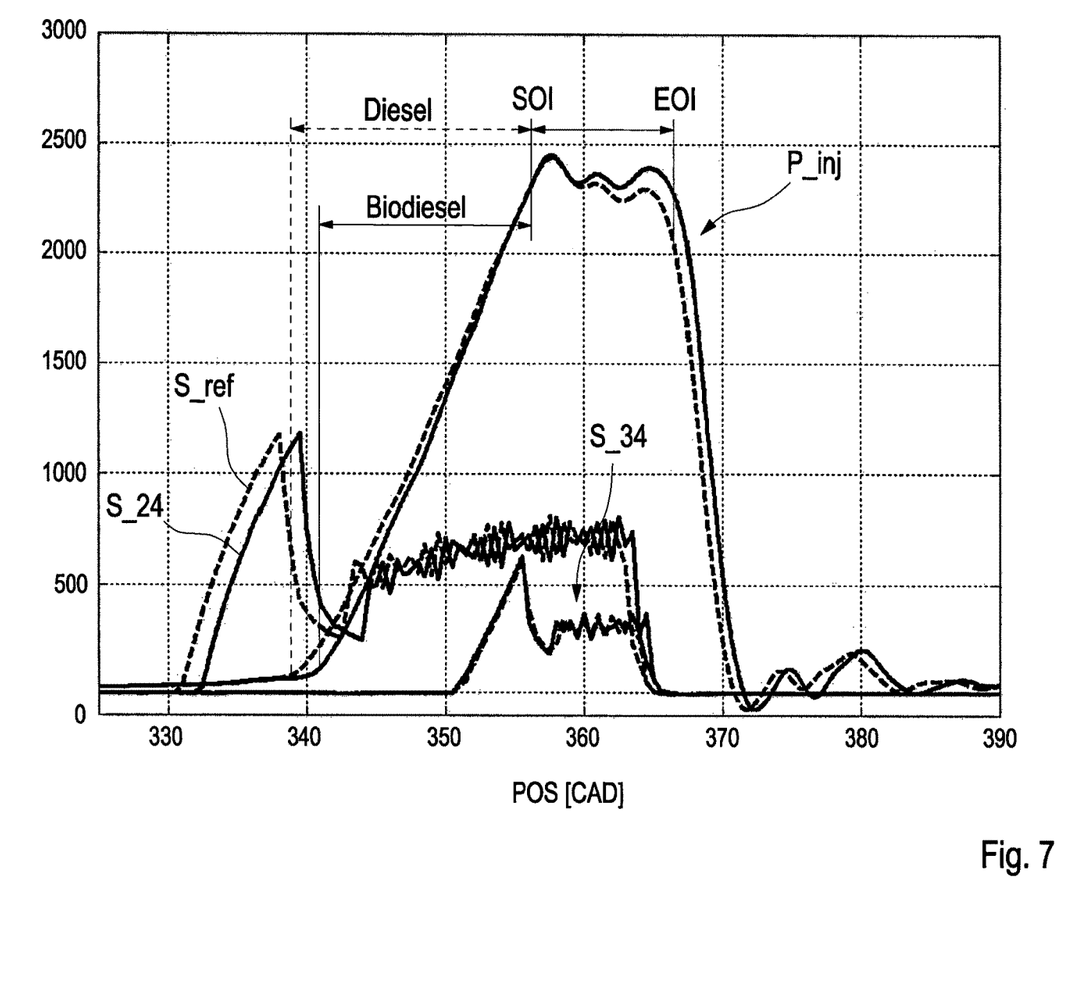
FIG. 7 a comparison of pressure signals of a unit-injector system for petrodiesel and for a fuel having a higher density and viscosity than petrodiesel for a system according to FIG. 6.

In FIG. 7 the solid line graphs refer to biodiesel and broken line graphs refer to standard petrodiesel. Biodiesel (as for instance RME) has a much higher viscosity and density compared to standard petrodiesel, and will therefore require a shorter pumping period. The higher the grade of RME blending is, the lower the "duty cycle", i.e. the pumping period, will be.

Figure 8:
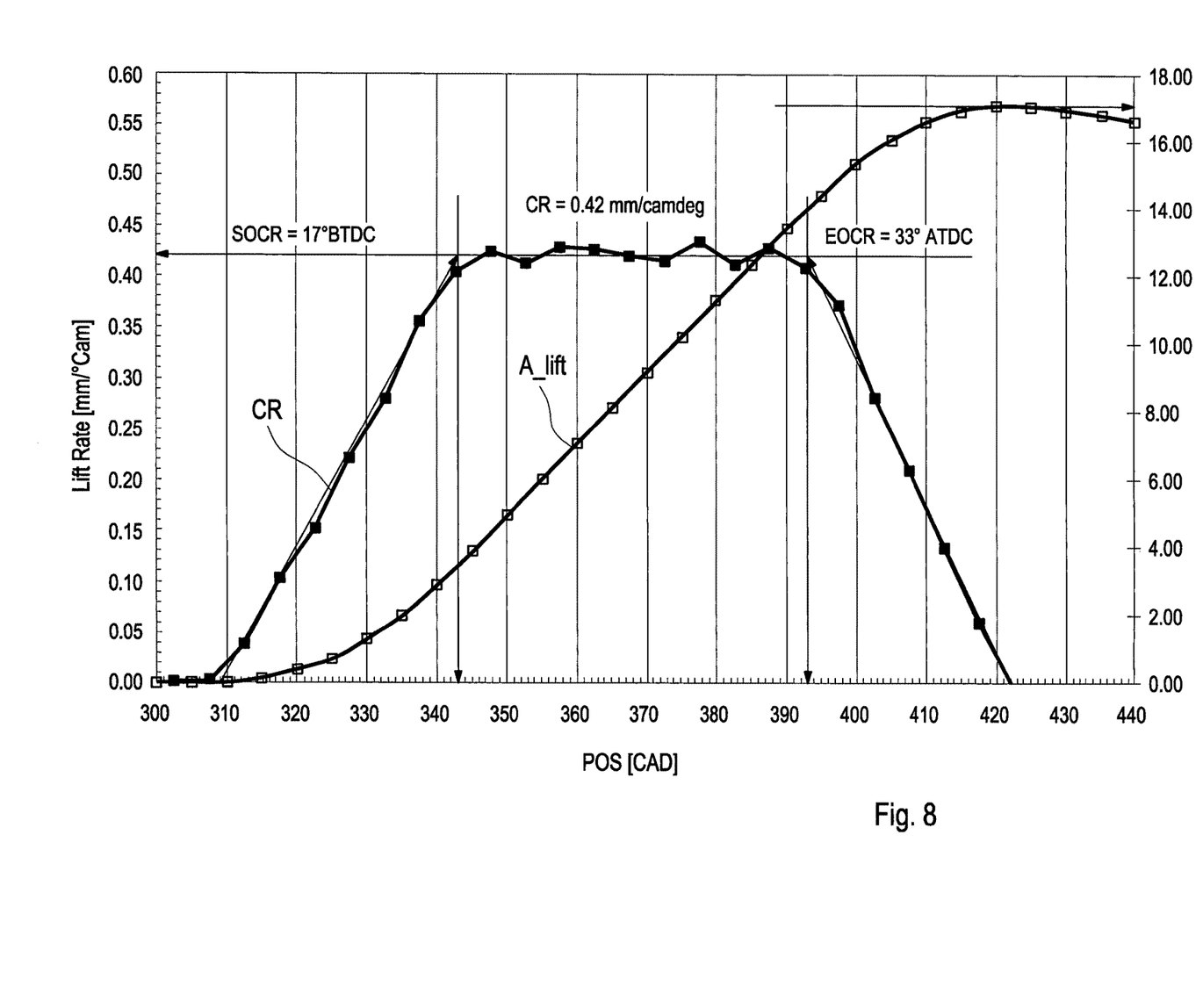
FIG. 8 a characteristic curve of a movement of a pumping element and a lift rate as a function of a crank angle position in a system of FIG. 7.

FIG. 7 depicts a comparison of the injection pressure p_inj for petrodiesel and for a fuel having a higher density and viscosity than petrodiesel, while FIG. 8 illustrates a movement of a pumping element and a lift rate CR as a function of a crank angle position POS. In FIG. 8 the movement of the pumping element is referred to as AJift (in the graph of the Figure shown as Lift in mm) showing an increase in the lift of the pumping element between approximately 300° and 420° POS with a nearly linear gradient in the middle, and the cam rate is shown as graph CR having a peak with a broad maximum between approximately 340° and 390° POS corresponding to the linear gradient of AJift, showing the lift rate of the pumping element (in the graph of the Figure shown as mm/° Cam—see left hand vertical coordinate in FIG. 8) as a function of a crank angle position POS shown in CAD (Crank Angle Degrees).

With a unit-injector system the pumping event starts before the fuel is injected into the combustion chamber 18. The point in time where the injection starts is also called SOI (SOI=Start Of Injection), see FIG. 7. The pumping ends simultaneously as the injection period ends. The point in time where the injection ends is also called EOI. The length of the build-up phase of the pressure before start of injection is defined as the NOP-angle (NOP=Needle Opening Pressure, i.e. the pressure at SOI). The pressure increase during the build-up phase of the pressure (NOP-angle) is relatively linear. The gradient of the pressure increase in the build-up phase is a function of cam lift rate (AJift in FIG. 8), engine speed, plunger diameter and fuel characteristics. The gradient is steeper with biodiesel for the same injection pressure p_inj. The difference of the pressure gradients in the build-up phase between pumping petrodiesel and biodiesel is a measure for the quality of the actual fuel.

For comparison, in FIG. 7 the timing signals S_ref and S_24 of the control valve 24 (FIG. 6) are shown for petrodiesel and for biodiesel, respectively.

The behaviour of the injection pressure p_inj during the injection period (injection duration) is dependent on the same parameters as the gradient of the pressure in the build-up phase but also of the nozzle flow number, which in turn is a result of the size and the number of nozzle holes of the injector 40. At EOI, the needle control (of needle valve 34) and the spill valve 24 deactivate and the remaining fuel in the pump chamber 22a (at pump 22) is pumped out into the low pressure circuit, i.e. into the low pressure fuel tank 12.

When the system starts, an injection pressure p_inj is established according to the parameters mapped in the control unit 60 (FIG. 6). As the gradient of the pressure in the build-up phase is dependent on the fuel quality, after a few cycles the gradient of the pressure in the build-up phase characteristic is established according to the fuel kind actually used in the system, which can be extracted by the pressure values monitored by pressure sensor 36 (FIG. 6).

The detection of a fuel quality for this system is possible from the gradient of the increase of the pressure p_inj during the build-up phase and/or via spill valve timing for a given NOP.

Advantageously, the method according to the invention can identify any mixture of biodiesel and standard diesel, so that a safe operation of the engine and the vehicle is possible.

The invention claimed is:

1. A method for determining a fuel quality of a fuel for a combustion engine, particularly for a diesel engine, wherein the fuel is conveyed from a low pressure fuel tank to a high-pressure volume, and injected into at least one cylinder of the combustion engine, wherein a control valve is provided for controlling directly or indirectly the amount of fuel injected into the at least one cylinder,
   wherein an actual value of a timing signal of the control valve is compared to a reference value of the timing signal of the control valve and a fuel quality parameter is derived from a difference between the actual value and the reference value of the timing signal of the control valve,
   wherein the timing signal of the control valve is refined with an actual value of a pumping period of a fuel pump conveying the fuel from the fuel tank to the combustion engine.

2. The method according to claim 1, wherein the fuel is conveyed from the fuel tank at a first pressure to the high-pressure volume at a pressure higher than the first pressure and injected into the at least one cylinder of the combustion engine, wherein the control valve is provided for limiting the fuel pressure in the high-pressure volume.

3. The method according to claim 1, wherein the timing signal of the control valve s refined with an actual value of the temperature of the fuel.

4. The method according to claim 1, wherein the reference value of the timing signal of the control valve derived from a set of characteristic curves for a reference fuel.

5. The method according to claim 1, wherein a fuel quality parameter is derived from a gradient of the pressure increase during a build-up phase of the pressure in the high-pressure volume compared to a reference value of the gradient of the pressure increase in the high-pressure volume.

6. The method according to claim 5, wherein a required pressure in the high-pressure volume is established via a closed loop control of the pressure in the high-pressure volume by adjusting the actual value of the tuning signal of the control valve and/or its operating duration.

7. The method according to claim 6, wherein in a unit-injector system a required pressure in the high-pressure volume is established via a closed loop control by adjusting the needle-opening pressure of an injector valve or by adjusting the actual value of the timing signal of the control valve and/or its operating duration.

8. The method according to claim 5, wherein the actual value of the pressure in the high-pressure volume is determined at constant engine torque.

9. The method according to claim 5, wherein the pressure in the high-pressure volume is refined with an actual value of the temperature of the fuel.

10. The method according to claim 5, wherein a reference value of the pressure in the high-pressure volume is derived from a set of characteristic curves for a reference fuel.

11. An arrangement for performing a method for determining a fuel quality of a fuel for a combustion engine, according to claim 1, wherein the fuel is conveyed from a low pressure fuel tank to a high-pressure volume, and injected into at least one cylinder of the combustion engine, wherein a control valve is provided for controlling directly or indirectly the amount of fuel injected into the at least one cylinder, wherein a control unit (60) is provided for comparing an actual value of a timing signal of the control valve to a reference value of the timing signal of the control valve and deriving a fuel quality parameter from a difference (AS) between the actual value and the reference value of the timing signal of the control valve, and for refining the timing signal of the control valve with an actual value of a pumping period of a fuel pump conveying the fuel from the fuel tank to the combustion engine.

12. The arrangement of claim 11, wherein a fuel quality parameter is derived from a gradient of the pressure increase during a build-up phase of the pressure (pjnj) in the high-pressure volume compared to a reference value of the gradient of the pressure increase in the high-pressure volume.

13. The arrangement according to claim 11, wherein the control valve is a spill valve for limiting a fuel pressure in the high-pressure volume of the common-rail injection system.

14. The arrangement according to claim 11, wherein a temperature sensor is provided for determining an actual value of the temperature of the fuel.

15. The arrangement according to claim 11, wherein a pressure sensor is provided for determining an actual value of the pressure in the high pressure volume and/or a pressure gradient related to the pressure in the high pressure volume.

16. The arrangement according to claim 11, wherein the high pressure volume is a rail of a common-rail injection system.

17. The arrangement according to claim 11, wherein the high pressure volume is a pump chamber of a fuel pump of a unit injector system.

18. A vehicle comprising an arrangement in accordance with claim 11.

19. Computer comprising a computer program adapted to perform a method according to claim 1 when the program is run on the computer.

20. Computer program product stored on a non-transitory computer readable medium, comprising a program adapted to perform a method according to claim 1.

* * * * *